United States Patent [19]
McGlothlin et al.

[11] Patent Number: 4,606,866
[45] Date of Patent: Aug. 19, 1986

[54] WETTABLE DEVICES OPERATIONAL WITH AQUEOUS LIQUID AND METHOD THEREFOR

[75] Inventors: Mark McGlothlin, Vernon Hills; Dennis Reisdorf, Crystal Lake; Robert Virag, Cary, all of Ill.

[73] Assignee: Baxter Travenol Laboratories, Inc., Deerfield, Ill.

[21] Appl. No.: 721,485

[22] Filed: Apr. 8, 1985

Related U.S. Application Data

[63] Continuation of Ser. No. 510,002, Jul. 1, 1983, abandoned.

[51] Int. Cl.$^4$ ................................................. B01F 3/04
[52] U.S. Cl. ........................................ 261/74; 73/293; 73/327; 116/227; 128/202.22; 261/66; 261/DIG. 65; 350/582
[58] Field of Search .................... 261/66, 104, 107, 74, 261/DIG. 65; 73/293, 327; 116/202, 227; 128/201.15, 202.22, 204.13; 350/359, 582, 584

[56] References Cited

U.S. PATENT DOCUMENTS

| | | | |
|---|---|---|---|
| Re. 23,085 | 2/1949 | Gunderson | 252/321 |
| 2,248,909 | 7/1941 | Russell | 165/133 |
| 2,328,551 | 7/1943 | Gunderson | 252/321 |
| 2,413,101 | 12/1946 | Delano | 202/234 |
| 2,469,729 | 5/1949 | Hunter | 165/1 |
| 3,291,198 | 12/1963 | Timson | 165/2 |
| 3,535,934 | 10/1970 | Rapata | 73/327 |
| 3,736,172 | 5/1973 | Delano et al. | 427/236 |
| 3,865,619 | 2/1975 | Pennewiss et al. | 350/582 X |
| 3,887,487 | 6/1975 | Camp et al. | 252/321 |
| 3,935,367 | 1/1976 | Merrill et al. | 350/582 X |
| 3,995,169 | 11/1976 | Oddon | 73/293 X |
| 4,038,650 | 7/1977 | Evans et al. | 73/293 X |
| 4,064,308 | 12/1977 | Laurin | 350/582 X |
| 4,287,756 | 9/1981 | Gallagher | 73/293 X |
| 4,303,601 | 12/1981 | Grimm et al. | 261/DIG. 65 |
| 4,353,799 | 10/1982 | Leonard | 210/321.3 |
| 4,354,984 | 10/1982 | Richardson et al. | 261/66 |
| 4,440,022 | 4/1984 | Masom | 73/293 |
| 4,468,567 | 8/1984 | Sasano et al. | 73/293 X |

OTHER PUBLICATIONS

Hawley, G. G.; *The Condensed Chemical Dictionary;* 8th Edition; Copyright 1971; Reinhold Co.; pp. 818, 907.

*Primary Examiner*—Richard L. Chiesa
*Attorney, Agent, or Firm*—Paul C. Flattery; Kay H. Pierce; John A. Caruso

[57] ABSTRACT

A humidifier (10) used in respiratory therapy is disclosed where the surface tension of a light probe (32) used therewith is maintained greater than the surface tension of the aqueous liquid used in the humidifier (10). Maintaining the surface tension of the light probe (32) greater than the surface tension of the aqueous liquid generally avoids erroneous indication of aqueous liquid level in the humidifier (10). Erroneous indications of liquid level can be caused by gas bubbles adhering to submerged portions of the light probe (32) or liquid droplets adhering to unsubmerged portions of the light probe (32). Surface tension of the light probe (32) can be maintained greater than surface tension of the aqueous liquid by coating the light probe (32) with a surface active agent, by subjecting the light probe (32) to corona discharge or plasma treatment, by coating the interior surface of the humidifier cannister (14) with an amount of surface active agent, by adding an amount of surface active agent to the aqueous liquid in the humidifier (10) or by any combination.

43 Claims, 6 Drawing Figures

Gas bubble formation or nucleation generally is caused by air or another gas fixing to a site and adhering to microscopic fissures, cavities, scratches and other surface irregularities. Generally, gas bubble formation occurs when the surface tension of the aqueous liquid is greater than the surface tension of the light probe.

Sometimes, beads and droplets of liquid adhere to unsubmerged portions of the light probe. These forms of liquid will refract internally reflected light away from the light probe. A dramatic loss of totally internally reflected light results, and there is an undesirable loss of the light signal necessary for the detection of liquid level. A light probe having an exposed end and having liquid droplets adhering thereto may refract enough internally reflected light away from the light pipe so that liquid is not maintained at an optimum level through controlled liquid replacement. Liquid droplet formation on unsubmerged portions of the light probe occurs when the surface tension of the condensate is greater than the surface tension of the light probe.

It would be desirable to alter the surface tension characteristics of an optical surface which is operational with aqueous liquids and which optical operation is impaired by the effects of the indices of refraction among the liquid, gases, and the optical surface.

It would be expedient to eliminate or greatly reduce the adherence of submerged gas bubbles to instruments operational with aqueous liquids whereby the operation is impaired by adherence of gas bubbles.

It would be advantageous to alter the surface tension characteristics of the surface of a light probe used in a humidifier container which would make the light probe surface tension greater than the aqueous liquid with which it is used in order that gas bubbles in the aqueous do not adhere to the light probe thereby producing erroneous indications of liquid level.

It would be advantageous to alter the interiors of containers enclosing the basic elements of a ventilator, humidifier device in order that the effect would be to render surfaces of enclosed elements more hydrophilic in order that microscopic beads and droplets of liquid do not adhere to unsubmerged portions of enclosed devices and in order that gas bubbles in the aqueous liquid do not adhere to submerged portions of the enclosed devices.

It would be expedient to eliminate or greatly reduce the adherence of beads and droplets of liquid to optical instruments whereby operation is impaired by adherence of liquid droplets.

It would be advantageous to alter the surface tension characteristics of an optical surface which is operational in an environment conducive to liquid droplet formation which operation is impaired by their effects on the refractive indices among the liquid, gases, and the optical surface because of the differences in the indices of refraction between the aqueous liquid and the optical surface.

It would be desirable to alter the surface tension characteristics of the surface of a light probe used in a humidifier container which would make the surface more hydrophilic in order that beads and droplets of liquid do not adhere to unsubmerged portions of the light probe but form a thin layer of liquid parallel to the surface of the probe so that internally reflected light is not refracted away from the light probe.

It also would be advantageous to provide a substantially non-toxic agent which may be added to an aqueous liquid whereby the formation of gas bubbles or liquid droplets is inhibited on instrumentation operational with the aqueous liquids. Operation of the instrument would not, thereby, be impaired by the adherence of submerged gas bubbles or droplets of liquid on unsubmerged portions of the instrument.

BRIEF SUMMARY OF THE INVENTION

The present invention provides for maintaining the surface tension of an optical surface, such as a light probe used in humidifier devices or the like, greater than the surface tension of aqueous liquids used therewith. Aqueous liquids generally are contained in cannisters of the humidifier devices. Maintaining this relationship between optical surfaces of the humidifier devices and aqueous liquids is accomplished by altering the surface tension characteristics of the light probe, the aqueous liquid or both so that the surface tension of the light probe is greater than that of the aqueous liquid with which it is used.

Preferably, a surface active agent (also referred to as a surfactant) is applied to the surface of the light probe or light pipe used in the humidifier container. Alternatively, a quantity of surface active agent can be added to the aqueous liquid used in the humidifier, a surface active agent can be applied to portions of the interior surface of the humidifier container, or the surface of the light probe can be subjected to plasma surface treating processes such as corona discharge. Plasma surface treating processes can be used alone or in combination with treatments involving use of a surfactant.

Submerged gas bubbles do not adhere to the surface of the light probe in a humidifier treated accordingly; hence, desired operation of the light probe is not impaired. When the end of the light probe is in contact with aqueous liquid, light is not internally reflected at the probe end but instead passes through the surface, continuing its path into the liquid.

Beads and droplets of liquid do not adhere to unsubmerged portions of the light probe in a humidifier treated accordingly, hence, desired operation of the light probe is not impaired. When the end of the light probe is not in contact with aqueous liquid, light is internally reflected at the probe end rather than being refracted away from the light probe. There would no longer be an undesirable loss of the light signal necessary for the detection of liquid level.

In addition to treating the light pipe or probe in the humidifier, an amount of surface active agent may be added to the liquid in the container. The formation of air bubbles in the liquid and on the submerged surfaces of instruments operating with the liquid would be reduced or eliminated. Formation of beads and droplets of liquid on unsubmerged surfaces of instruments operating with the liquid would be reduced or eliminated. Surface tension characteristics of the aqueous liquid also can be altered by coating portions of the interior surfaces of the humidifier container.

In accordance with this invention, one may apply a surface active agent to the surface of a light probe or light pipe made of a transparent hydrophobic plastic such as LEXAN® thermoplastic. (LEXAN® is a registered trademark of the General Electric Company for polycarbonate thermoplastic), a polyacrylate thermoplastic, or another thermoplastic. Application of a surface active agent to the light probe makes the surface more hydrophilic. It is known in the art which surface active agents make more hydrophilic the particular surface materials involved. For example, with a LEX-

WETTABLE DEVICES OPERATIONAL WITH AQUEOUS LIQUID AND METHOD THEREFOR

This application is a continuation of application Ser. No. 510,002 filed July 1, 1983, now abandoned.

FIELD OF THE INVENTION

This invention generally relates to maintaining the surface tension of instruments, operational with aqueous liquids, greater than the surface tension of the aqueous liquids they are used with. This is accomplished by altering the surface tension characteristics of the instrument, the aqueous liquid or both.

Surfaces of instruments operational with aqueous liquids can be made more hydrophilic. This limits adherence of submerged gas bubbles to the surfaces and reduces the likelihood of impaired operation. Also, the invention generally relates to making more hydrophilic, optical surfaces whose operation is impaired by the adherence of liquid droplets to unsubmerged surfaces. Similar results can be achieved by decreasing the surface tension of the aqueous liquids below the surface tension of the instruments or devices. Adherence of gas bubbles to submerged surfaces or liquid droplets to unsubmerged surfaces is impaired.

The invention particularly relates to ventilator, humidifier devices useful in humidifying inhalation gas being administered to patients under respiratory therapy. Liquid level sensing devices that automatically replenish liquid, to provide generally optimum humidification conditions, specifically benefit from this invention. This invention relates to improvements in the automatic liquid level sensing device. The improvements impair the adherence of gas bubbles, submerged in aqueous liquids, to the liquid level sensing means of the device by using surfactants in the aqueous liquids, treating the device, or both. Adherence of gas bubbles to the liquid level sensing means can result in erroneous indications of liquid level.

Use of surfactants, surface treating the device, or both, also impairs adherence of beads and droplets of liquid to the liquid level sensing means. Beads and droplets of liquid can cause erroneous indications of liquid level as well.

In addition, containers enclosing the basic elements of the ventilator, humidifier device and containing the aqueous liquid can be treated using surfactants. Treating interiors of the containers with a surfactant impairs adherence of gas bubbles to elements submerged in the aqueous liquids and contained in the container. Use of a surfactant treated container also impairs adherence of liquid droplets to elements within the container.

BACKGROUND OF THE INVENTION

U.S. Pat. No. 4,303,601, *Ventilator Humidifier*, to Grimm, et al. [hereinafter cited as Grimm], discloses a ventitilator, humidifier device for gases having an automatic liquid level sensing device. Coupled to the liquid level sensing device is an automatically operated valve which allows added liquid to flow into a ventilator, humidifier system thereby maintaining liquid at a desired optimum level. A removable cannister for containing the liquid has a closure defining a gas inlet and a gas outlet as part of the flow line to the breathing apparatus of the patient. A tubular wick inside the cannister soaks up the aqueous liquid.

In Grimm, liquid is maintained typically at a relatively low level within the cannister so that the circulating gas is humidified primarily from the tubular wick. More liquid may be added to the cannister, for example, from a solution bag of sterile water, through a tube into the cannister. The tube generally passes through a solenoid switch which pinches the tubing shut to stop flow and intermittently opens the tube when a low liquid level is sensed. A light probe is positioned in the cannister so that visible light, or typically light from the infrared portion of the spectrum, passes down the probe and is reflected from a conical-shaped end of the probe in the event that the liquid level is low. A sensor detects the reflected light and actuates the solenoid to open the switch. Liquid then flows into the cannister until reflected light is no longer detected.

U.S. Pat. No. 4,354,984, *Liquid Level Controller for a Humidifier*, to Richardson, et al. [hereinafter cited as Richardson], discloses a tube clamp assembly for an oxygen gas humidifier used in respiratory therapy. The clamp assembly is part of a control system for controlling the flow of replacement liquid to the humidifier cannister. A light probe and sensor are a part of the liquid level control system.

Typically, the light probe, or light pipe, used to detect liquid level, is made from a hydrophobic, thermoplastic material. The liquid level sensing probe has an end which may be defined by a conical surface if desired, or any other surface which provides angled surfaces positioned to permit light passing into the highly transparent probe and toward the end surface to be reflected back up the probe in a returning beam of light after striking at reflection points.

When the end of the light probe of the Grimm patent is in contact with liquid, the refractive conditions at the end surface are changed because of the relatively slight difference in the index of refraction of liquid with respect to the light probe so that the light beam is not reflected. Instead, the light passes through the surface, continuing its downward path so that there is no significant reflective light beam. Accordingly, the presence or absence of contacting liquid at the end surface can be indicated by the presence or absence of a reflected light beam.

A light sensor, in the Grimm patent, communicating with the other end of the light probe detects the reflected light. When a reflected light beam is detected, generally indicating a low liquid level, the light sensor actuates a solenoid to open a valve permitting liquid flow through tubing to the cannister. The liquid level rises until the end surface of the probe is covered. At this point, the reflected beam terminates, thus deactivating the light sensor and causing the solenoid to deactivate. This, in turn, closes the valve, shutting off liquid flow.

At times, submerged air or other gas bubbles adhering to the end surface of the light probe may cause the light beam to be reflected back through the light probe and detected by the light sensor even when the liquid level is adequate. The light sensor would, in turn, actuate the solenoid to open the valve, permitting liquid to flow into the cannister. The addition of liquid, however, when submerged air or other gas bubbles adhere to the light pipe, would not cause deactivation of the solenoid. Liquid would continue to flow into the cannister until a local disturbance dislodged the adhered gas bubbles, until the liquid source was depleted, or until a specified time period elapsed.

AN ® or polyacrylate material light probe, the surface active agent may consist essentially of a non-ionic ester of a carbohydrate moiety and an organic monoacid of 8 to 30 carbon atoms. It has been found that this particular family of surface active agents is physiologically compatible, easily metabolized and is subject to a low degree of toxic reaction.

An example of the surface active agent of this invention which is preferred is a mixture of monoesters of sorbitan with capric, lauric, myristic, palmitic or oleic acids or all of them. As a specific example, the mixture may include the following typical weight percentages of monoesters, sold as SPAN ® 20 surfactant by ICI Americas, Inc. (SPAN ® is a registered trademark of ICI Americas, Inc.): sorbitan caprate 1.1%; sorbitan laurate 43.5%; sorbitan myristate 27.8%; sorbitan palmitate 19.2%; and sorbitan oleate 8.4%. However, other analogous esters can be used, pure or mixed, preferably monoesters of carbohydrate such as sorbitan, glucose, fructose, or other metabolizable carbohydrates of preferably 5 to 6 carbon atoms. The organic monoacids used of 8 to 30, and preferably 10 to 20, carbon atoms, may be any appropriate monoacid which reacts with the carbohydrate moiety to preferably form a monoester, that is, 1 carbohydrate molecule reacted with 1 monoacid molecule. The acids which may be used include those described above or others such as tridecanoic acid, or mixed acids such as linseed oil acids, to provide an appropriate hydrophobic portion, combined with the hydrophilic carbohydrate moiety to form the desired surface active agent. Preferably, a light pipe or other instrument whose operation with water may be impaired by the adherence of air bubbles thereto can be coated with the surface active agent of this invention.

Alternatively, an amount of these surface active agents may be added to the aqueous liquid or used to coat portions of the interior of the humidifier cannister thereby inhibiting the formation of gas bubbles in the liquid which would adhere to submerged surfaces and minimizing or greatly reducing liquid droplet formation on unsubmerged surfaces. Preferred surface active agents for direct addition to an aqueous liquid contained in a humidifier or for coating surfaces are SPAN ® 20 surfactant, ethoxylated sorbitan monolaurates, for example, polyoxyethylene (20) sorbitan monolaurate, sold by ICI Americas, Inc. as TWEEN ® 20 surfactant, and polyoxyethylene (4) sorbitan monolaurate sold as TWEEN ® 21 surfactant by ICI Americas, Inc.

Surface tension on the light probe can be maintained greater than surface tension of the aqueous liquids they are used with by treating the light probe using conventional plasma generators such as corona discharge devices. Corona discharge or plasma generator treating processes deliver results essentially similar to coating the light pipe with SPAN ® 20 surfactant. With these treatments, the light probes are exposed to an ionized gas such as oxygen that alters the surface of the light probe, thereby increasing surface energy. The surface of the light probe becomes more hydrophilic.

It should be appreciated that the provisions of applying a surfactant to the light probe, corona discharge treating of the light probe, plasma generator treating of the light probe, adding surfactant to the aqueous liquids in the humidifier container or surfactant coating the interior of the humidifier container can be used alone or in all their possible combinations with the object being to maintain the surface tension of the light probe greater than the surface tension of the aqueous liquids they are used with.

BRIEF DESCRIPTION OF THE DRAWINGS

For a more complete understanding of this invention reference should now be had to the embodiment illustrated in greater detail in the accompanying drawings.

In the drawings.

DESCRIPTION OF THE PREFERRED EMBODIMENT

Figure 1:
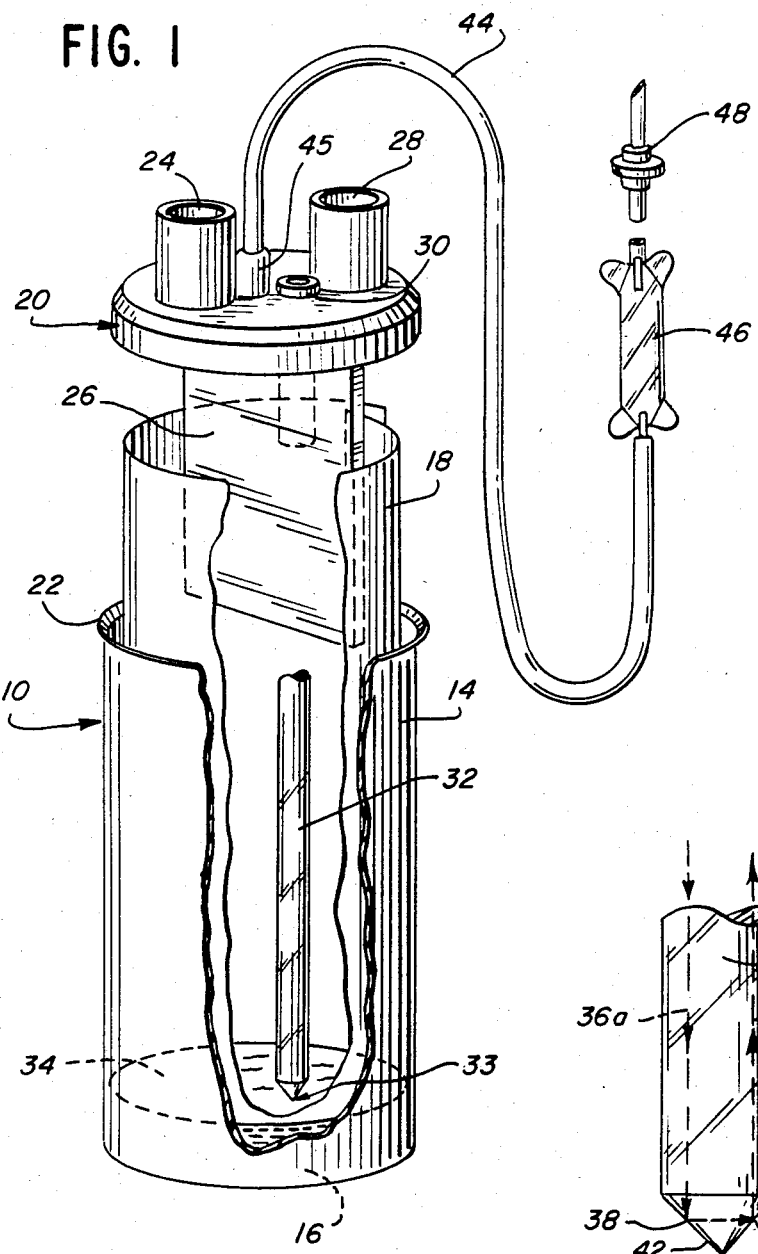
FIG. 1 is an exploded perspective view of a humidifier portion of a ventilator humidifier device showing the light probe element therein.

Turning now to the drawings, FIG. 1 is an exploded perspective view of a humidifier cannister illustrating the basic elements contained therein. Humidifier element 10 is adapted for insertion into the well of a heater assembly. Humidifier element 10 comprises a seamless, open mouthed metal cannister 14 defining cylindrical walls and a closed bottom end 16. Cannister 14 simply may be a commercial beverage can purchased from a can manufacturer at low cost.

Wick means 18 may be made from a sheet of material rolled up into a structure which preferably is generally cylindrical, wick means 18 being made of a porous paper material or the like. Accordingly, wick means 18 absorbs water in the bottom of cannister 14 and presents it in dispersed, high surface area form to gases flowing through cannister 14.

Closure 20 may be made of a single piece of molded plastic. It is adapted to fit in tight, sealing manner about mouth 22 of cannister 14. Closure 20 defines a gas inlet port 24. Baffle 26 is provided to prevent shunting of non-humidified gas out of outlet aperture port 28, which is defined as shown by closure 20. Both inlet port 24 and outlet 28 are adapted for attachment to flexible gas flow tubing of conventional design for a patient breathing circuit or the like.

Closure 20 also defines light access port 30 through which may extend translucent probe means 32. Probe means 32 may be made of highly transparent polycarbonate plastic, polyacrylate plastic, polysulfanone plastic, or the like. Probe means 32 extends through cannister 14 preferably to at least the remotest third of the cannister interior from closure 20 to serve as a liquid level measuring means as described below. It is preferred that liquid level 34 be maintained in the lower third of cannister 14. This exposes a large surface area of wick means 18, which is preferably of essentially the same height as that of cannister 14, to take up the liquid and to expose a large surface area of wet wick means 18 to dry gases entering through inlet port 24, for improved humidification due to the large surface area.

Turning further to the structure of humidifier element 10, in FIG. 1, flexible tubing 44 is connected to port 45 in closure 20 to supply liquid to humidifier element 10. A standard drip chamber 46 is provided adjacent the free end of tubing 44, which terminates in a standard hollow piercing spike 48, for penetration into a conventional liquid supply container, for example, a bottle or bag of sterile water sold by Travenol Laboratories, Inc., of Deerfield, Illinois.

Figure 2:
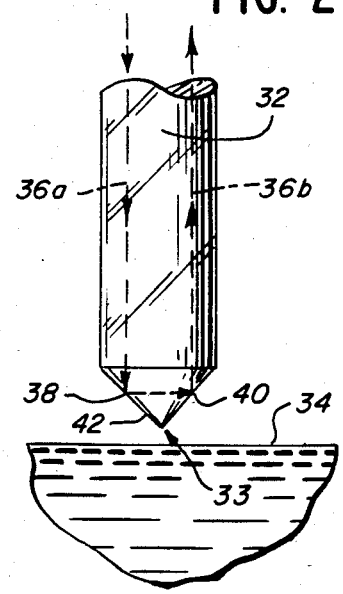
FIG. 2 is an enlarged, fragmentary elevational view of the remote end of the light-transmitting probe unsubmerged, showing light being reflected.

Liquid level light probe means 32 defines end 33 which may be defined by a conical surface if desired, or any other surface which provides angled surfaces. Referring to FIG. 2, light beam 36a passing in the transparent probe means 32 toward end surface 33 is reflected in a returning beam of light 36b after striking at two reflection points 38, 40, causing the light beam to make two 90° angle reflective turns. Conical surface 42 preferably defines an angle of 45° to the axis of probe 32 and particularly incoming light beam 36a.

A light sensor at light access port 30 detects the reflected light beam 36b. When reflected light beam 36b is detected, generally indicating low liquid level 34, the light sensor activates a solenoid to open a valve permitting liquid flow through tubing into cannister 14. The solenoid is deactivated, thereby closing the valve, when liquid level 34 is above end 33 of light probe 32 as is illustrated in FIG. 3.

Figure 4:
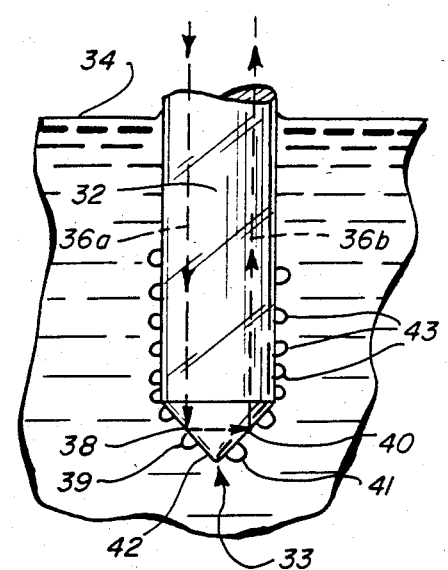
FIG. 4 is an enlarged, fragmentary elevational view of the remote end of the light-transmitting probe submerged in liquid, showing light being reflected due to the presence of gas bubbles.

Light beam reflection, as shown in FIG. 4, takes place when gas bubbles 43 adhere to end 33 of probe 32. As can be seen, reflection points 38, 40 are points having effected indices of refraction caused by the difference in the index of refraction of the liquid with respect to the gas of bubbles 39 and 41. Light beam 36b is reflected back to the light sensor at light access port 30 even though there is a sufficient liquid level 34. The solenoid is activated to open the valve, permitting liquid to flow into cannister 14. In this instance, addition of liquid would not cause deactivation of the solenoid. Liquid would continue to flow into cannister 14 until a local disturbance dislodged gas bubbles 39, 41, until the liquid source was depleted, or until a specified time period elapsed.

Plasma treatment such as corona discharge treatment of the surface of probe 32, addition of a surface active agent to the surface of probe 32, addition of a surface active agent to the liquid, addition of a surface active agent to portions of the interior surface of cannister 14, or combinations of these alternatives inhibit the adherence of gas bubbles to the surface of submerged light probe 32. Such treatments, or combinations thereof, additionally inhibit liquid droplet formation on unsubmerged portions of light probe 32.

Figure 3:
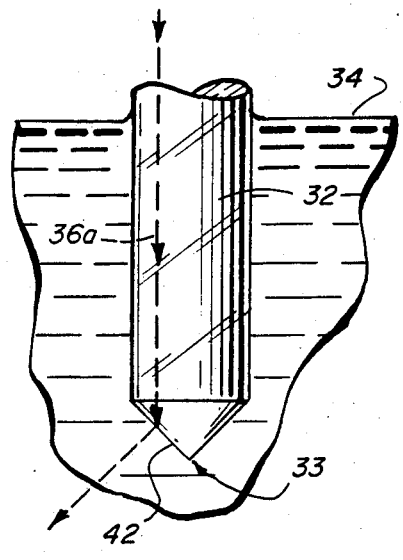
FIG. 3 is an enlarged, fragmentary elevational view of the remote end of the light-transmitting probe submerged in liquid, showing light passing into the water.

FIG. 3 is illustrative of the effect which surface active agents or surface treatments have on the submerged portion of light probe 32. The surface of light probe 32 can be coated with SPAN ® 20 surfactant earlier described. SPAN ® 20 surfactant can be used to coat portions of the interior surface of cannister 14 or it can be added to the liquid in cannister 14. Amounts of TWEEN ® 20 or TWEEN ® 21 surfactants can be used to coat surfaces or added to the liquid in cannister 14 to provide similar results. Also, it is believed that quaternary ammonium compounds will have similar surface effects.

When end 33 of the probe is in contact with liquid and gas bubbles are not present on the surface of the probe, the refractive conditions at conical surface 42 are effected because of the difference in the index of refraction of the aqueous liquid with respect to light probe 32, so that light beam 36a is not reflected in the path indicated in FIG. 4. Light beam 36a instead passes through surface 42, continuing its downward path, so that there is no significant reflected light beam. Accordingly, the presence or absence of contacting liquids at conical end surface 42 can be indicated by the presence or absence of a reflected light beam 36b. When submerged air bubbles adhere to light probe 32, erroneous indications of liquid level, however, will be perceived.

To inhibit the formation of gas bubbles on light probe 32, the surface of light probe 32 can be subjected to a plasma treatment such as corona discharge. Corona discharge and other plasma treatments of light probe 32 alter the surface and increase the surface energy. It is also believed that these treatments assist in removing hydrophobic contaminates and also slightly oxidize the surface. For example, the surface tension on a polycarbonate light probe can be changed from 30–40 dynes per centimeter to greater than 72 dynes per centimeter. The surface of the polymer, thereby, becomes more hydrophilic.

Figure 5:
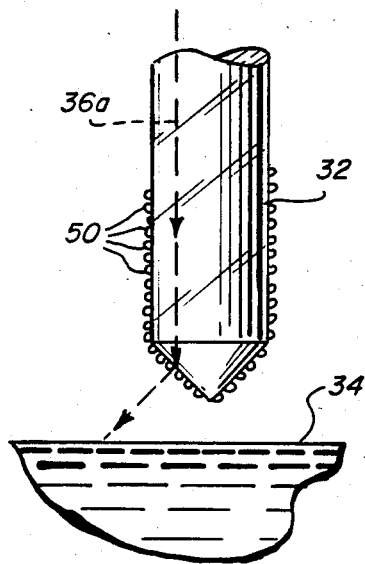
FIG. 5 is an enlarged, fragmentary elevational view of the remote end of the light-transmitting probe unsubmerged, with liquid condensate droplets thereon, showing light being refracted away from the probe.

Similar problems of erroneous indications of liquid level 34 in cannister 14 also can be caused by liquid droplet formation on the surface of light probe 32. FIG. 5 illustrates light probe 32 above liquid level 34. Liquid droplets 50 are shown adhering to the surface of light probe 32. Light beam 36a travels down light probe 32 and upon encountering liquid droplets 50 is refracted out of light probe 32 instead of being reflected back upward. A false indication of sufficient liquid level would be perceived. Liquid in cannister 14 would continue to be depleted until liquid droplets 50 were evaporated or shaken loose. Risk inheres that a patient would receive insufficiently humidified oxygen or inhalation gas.

Figure 6:
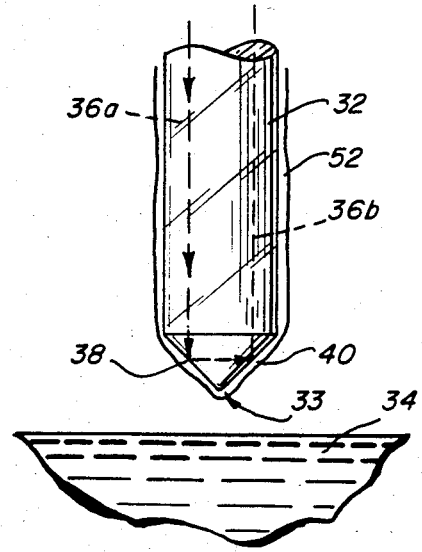
FIG. 6 is an enlarged, fragmentary elevational view of the remote end of the light-transmitting probe unsubmerged, with a monolayer of condensate thereon showing light being internally reflected.

Treatment of the surface of light probe 32 will inhibit liquid droplet formation. Light probe 32 can be subjected to the corona discharge or plasma treatments earlier described. Also, light probe 32 can be coated with SPAN ® 20 surfactant. Similar results of inhibiting liquid droplet formation on light probe 32 can be accomplished by the addition of TWEEN ® 20 or TWEEN ® 21 surfactants to the liquid in cannister 14 or by coating portions of the interior surface of cannister 14 with surfactants. Thereafter, liquid beads do not form but generally "sheet" or form a thin layer of liquid parallel to the probe surface. Internally reflected light is not refracted away from light probe 32. False indications of sufficient liquid level are avoided. FIG. 6 illustrates, in exaggerated detail, thin liquid layer 52 on light probe 32. Light beam 36a is reflected at reflection points 38, 40 and light beam 36b progresses to the light detector/solenoid combination. The solenoid thereafter will open the valve allowing liquid to flow into cannister 14 until sufficient liquid level is established.

The examples below are offered for illustrative purposes, and are not intended to limit the invention of this application, which is defined in the claims below.

EXAMPLE 1

A LEXAN ® polycarbonate material light probe of known configuration as disclosed in the Grimm patent was subjected to a plasma treatment. A plasma generator manufactured by Sorenson Research, Inc., was used to provide the surface plasma treatment. This equipment is operated on an inductive coupled principle. Several light probes were inserted into the evacuated cylinder of this device. Operating pressures of this device were between 0.1 to 10 mm Hg. The cylinder of the device is surrounded by an aluminum coil which generated a radio frequency field at 13.5 megahertz for 1 to 3 minutes. Air was the plasma medium and is the preferred plasma medium; however, it is believed that other gases will deliver similar results. A treated light probe and an untreated light probe were observed in a humid atmosphere, that is, suspended in vapor from boiling water and thereafter submerged. No beads or droplets of aqueous liquid appeared on the unsubmerged surfaces of the treated light probe. Liquid sheeted as opposed to beaded on the unsubmerged surfaces of the treated probe. Beads of liquid appeared on the unsubmerged surfaces of the untreated light probe. Little or no entrapment of gas bubbles was observed on submerged surfaces of the treated light probe when suspended in boiling water. Relatively substantial entrapment of gas bubbles was observed on submerged surfaces of the untreated light probe suspended in boiling water.

EXAMPLE 2

Corona discharge treatment was performed by using a portable, hand-held, high frequency electrode to create an ionized air atmosphere over the surface of LEXAN ® polycarbonate material light probes. The conventionally available "Spark-Tester", Model BD-20, manufactured by Electro-Technic Products, Chicago, Ill., was used. This unit operates at an average of 2 megahertz with a spark discharge ranging between 15,000 to 50,000 volts depending on the distance between the electrode and the light probe. The electrode was brushed over the surface of individual light probes to within ⅛ inch to 1 inch allowing the spark and corona to cover the entire tip and shaft of light probe for a period ranging from 5 to 60 seconds. The corona discharge treatment was performed at ambient pressures, and it was performed in air; however, it is believed that other gases will deliver similar results. A treated light probe and an untreated light probe were observed in a humid atmosphere, that is, suspended in vapor from boiling water and thereafter submerged. No beads or droplets of aqueous liquid appeared on the unsubmerged surfaces of the treated light probe. Liquid sheeted as opposed to beaded on the unsubmerged surfaces of the treated probe. Beads of liquid appeared on the unsubmerged surfaces of the untreated light probe. Little or no entrapment of gas bubbles was observed on submerged surfaces of the treated light probe when suspended in boiling water. Relatively substantial entrapment of gas bubbles was observed on submerged surfaces of the untreated light probe suspended in boiling water.

EXAMPLE 3

A LEXAN ® polycarbonate material light probe was dipped in a mixture of the following volume percentages: 10% SPAN ® 20 surfactant and 90% isopropyl alcohol. The isopropyl alcohol solvent was allowed to evaporate. A treated light probe and an untreated light probe separately were observed in a humid atmosphere, that is, suspended in vapor from boiling water and thereafter submerged. No beads or droplets of aqueous liquid appeared on the unsubmerged surfaces of the treated light probe. Liquid sheeted as opposed to beaded on the unsubmerged surfaces of the treated light probe. Beads of liquid appeared on the unsubmerged surfaces of the untreated light probe. Little or no entrapment of gas bubbles was observed on submerged surfaces of the treated light probe when separately suspended in boiling water. Relatively substantial entrapment of gas bubbles was observed on submerged surfaces of the untreated light probe separately suspended in boiling water.

EXAMPLE 4

A LEXAN ® polycarbonate material light probe was dipped in a mixture of the following volume percentages: 5% TWEEN ® 20 surfactant and 95% isopropyl alcohol. The isopropyl alcohol solvent was allowed to evaporate. A treated light probe and an untreated light probe separately were observed in a humid atmosphere, that is, suspended in vapor from boiling water and thereafter submerged. No beads or droplets of aqueous liquid appeared on the unsubmerged surfaces of the treated light probe. Liquid sheeted as opposed to beaded on the unsubmerged surfaces of the treated light probe. Beads of liquid appeared on the unsubmerged surfaces of the untreated light probe. Little or no entrapment of gas bubbles was observed on submerged surfaces of the treated light probe when separately suspended in boiling water. Relatively substantial entrapment of gas bubbles was observed on submerged surfaces of the untreated light probe separately suspended in boiling water.

EXAMPLE 5

A LEXAN ® polycarbonate material light probe was dipped in a mixture of the following volume percentages: 5% TWEEN ® 21 surfactant and 95% isopropyl alcohol. The isopropyl alcohol solvent was allowed to evaporate. A treated light probe and an untreated light probe separately were observed in a humid atmosphere, that is, suspended in vapor from boiling water and thereafter submerged. No beads or droplets of aqueous liquid appeared on the unsubmerged surfaces of the treated light probe. Liquid sheeted as opposed to beaded on the unsubmerged surfaces of the treated light probe. Beads of liquid appeared on the unsubmerged surfaces of the untreated light probe. Little or no entrapment of gas bubbles was observed on submerged surfaces of the treated light probe when separately suspended in boiling water. Relatively substantial entrapment of gas bubbles was observed on submerged surfaces of the untreated light probe separately suspended in boiling water.

EXAMPLE 6

Into a cannister for the humidifier was dropped 0.5 cc of SPAN ® 20 surfactant. The cannister was filled with water to approximately the half full level. A cannister similarly filled with water but without surfactant therein was observed alongside the treated cannister. Little or no entrapment of gas bubbles was observed on surfaces of the light probe submerged in boiling water in the treated cannister. Relatively substantial entrapment of gas bubbles was observed on surfaces of the light probe submerged in boiling water in the untreated cannister.

EXAMPLE 7

Equivalent results may be obtained when a LEXAN ® polycarbonate material light probe is dipped into a mixture having the following volume percentages: 10% SPAN ® 20 surfactant and 90% isopropyl alcohol, and 0.5 cc of SPAN 20 surfactant is added to the cannister of the humidifier. The cannister would then be filled approximately half full with water. When observed in a humid atmosphere, that is, suspended in vapor from boiling water and thereafter submerged, no beads or droplets of aqueous liquid will appear on the unsubmerged surfaces of the light probe. Liquid will sheet as opposed to bead on the unsubmerged surfaces of the light probe in the treated system. Little or no entrapment of gas bubbles will be observed on submerged surfaces of the light probe suspended in boiling water in the treated system.

What is claimed is:

1. The method of treating an exterior optical surface of an optical probe having light passing therein operational with aqueous liquids, comprising the step of selectively maintaining the surface tension of the optical surface greater than the surface tension of the aqueous liquid used therewith, with a surface active agent which is a physiologically compatible, easily metabolized, low toxic reaction means, thereby inhibiting the adherence of gas bubbles to submerged portions of the optical surface to allow said light passing therein not to be reflected and thereby further inhibiting the formation of liquid droplets to unsubmerged portions of the optical surface to allow said light passing therein to be reflected.

2. The method of claim 1 wherein the surface tension of the exterior of the optical surface of said optical probe is maintained greater than the surface tension of the aqueous liquid by applying a coating of surface activd agent, which is physiologically compatible with said aqueous liquid and is easily metabolized and has a low degree of toxic reaction, to the exterior of the optical surface of said optical probe.

3. The method of claim 2 in which the exterior optical surface of the optical probe is used in a humidifier for gases and the selective maintenance of the surface tension of the optical surface greater than the surface tension of the aqueous liquid is provided to allow the light in said probe to be reflected/ not reflected according to the humidifier's needs to thereby maintain sufficiently humidified oxygen or inhalation gas.

4. The method of claim 3 in which said surface active agent consists essentially of non-ionic ester of a carbohydrate moiety and an organic monoacid of 8 to 30 carbon atoms which is physiologically compatible with said aqueous liquid and is easily metabolized and has a low degree of toxic reaction.

5. The method of claim 3 in which said surface active agent is a mixture of sorbitan monoesters which is physiologically compatible with said aqueous liquid and is easily metabolized and has a low degree of toxic reaction.

6. The method of claim 3, wherein said light probe is made of a hydrophobic plastic material.

7. The method of claim 1 wherein the surface tension of the exterior of the optical surface of said optical probe is maintained greqter than the surface tension of the aqueous liquid by subjecting the optical surface face to plasma treatment which is physiologically compatible with said aqueous liquid while providing no toxic reaction therewith.

8. The method of claim 3 in which the exterior optical surface of the optical probe is used in a humidifier for gases and the selective maintenance of the surface tension of the optical surface greater than the surface tension of the aqueous liquid is provided to allow the light in said probe to be reflected/not reflected according to the humidifier's needs to thereby maintain sufficiently himidified oxygen or inhalation gas.

9. The method of claim 8, wherein said light probe is made of a hydrophobic plastic material.

10. The method of claim 1 wherein the surface tension of the exterior of the optical surface of said optical probe is maintained greater than the surface tension of the aqueous liquid by subjecting the optical surface to corona discharge treatment which is physiologically compatible with said aqueous liquid while providing no toxic reaction therewith.

11. The method of claim 1 wherein the surface tension of the exterior of the optical surface of said optical probe is maintained greater than the surface tension of the aqueous liquid by adding an amount of surface active agent which is physiologically compatible with said aqueous liquid and is easily metabolized and has a low degree of toxic reaction, to the aqueous liquid.

12. The method of claim 11 in which said surface active agent consists essentially of an ethoxylated non-ionic ester of a carbohydrate moiety and an organic monoacid of 8 to 30 carbon atoms which is physiologically compatible with said aqueous liquid and is easily metabolized and has a low degree of toxic reaction.

13. The method of claim 11 in which said surface active agent is a mixture of ethoxylated sorbitan monoesters which is physiologically compatible with said aqueous liquid and is easily metabolized and has a low degree of toxic reaction.

14. The method of claim 1 in which the exterior optical surface of the optical probe is used in a humidifier for gases and the selective maintenance of the surface tension of the optical surface greater than the surface tension of the aqueous liquid is provided to allow the light in said probe to be reflected/not reflected according to the humidifier's needs to thereby maintain sufficiently humidified oxygen or inhalation gas.

15. The method of claim 14, wherein said optical probe is made of a hydrophobic plastic material.

16. The method of claim 1 wherein the exterior optical surface of the optical probe and aqueous liquid are contained in a container and wherein the surface tension of the optical surface ia maintained greater than the surface tension of the aqueous liquid by applying a coating of surface active agent to at least a portion of the interior surface of the container, said surface active agent being physiologically compatible with said aqueous liquid and is easily metabolized and has a low degree of toxic reaction.

17. The method of claim 16 additionally comprising the step of applying a coating of surface active agent to the exterior optical surface of the optical probe.

18. The method of claim 17 in which the exterior optical surface of the optical probe is used in a humidifier for gases and in which said surface active agent is a mixture of sorbitan monoesters and the selective maintenance of the surface tension of the optical surface greater than the surface tension of the aqueous liquid is provided to allow the light in said probe to be reflected/not reflected according to the humidifier's needs to thereby maintain sufficiently humidified oxygen or inhalation gas.

19. The method of claim 18, wherein said light probe is made of a hydrophobic plastic material.

20. In a humidifier for gases having a cannister defining a well, a closure sealing the cannister, the closure defining a light access port, and transparent probe means communicating with the light access port, and extending into the cannister, the transparent probe means defining an end surface within the cannister interior which includes angled surfaces positioned to permit light passing into said transparent probe means toward the end surface to be reflected again up the probe away from the end surface when the end surface is out of contact with aqueous liquid, and the light to be transmitted through the end surface when the probe is in contact with the aqueous liquid, the improvement comprising:

said light probe having a surface tension maintained greater than the surface tension of the aqueous liquid by having been treated with a surface active agent whereby gas bubbles in the aqueous liquid are inhibited from adhering to submerged surfaces of the light probe to allow said light passing therein not to be reflected and whereby liquid droplets are inhibited from adhering to unsubmerged portions of the light probe to allow said light passing therein to be reflected and said surface tension being maintained with said surface active agent which is a physiologically compatible, easily metabolized low toxic reaction means to maintain sufficiently humidified oxygen or inhalation gas.

21. The humidifier of claim 16 wherein said light probe is made of polycarbonate thermoplastic.

22. The humidifier of claim 20 wherein said light probe has a surface active agent which is physiologically compatible with said aqueous liquid and is easily metabolized and has a low degree of toxic reaction applied thereto in order that the surface tension of the light probe is maintained greater than the surface tension of the aqueous liquid to allow the light in said probe to be reflected/not reflected according to the humidifier's needs to thereby maintain sufficiently humidified oxygen or inhalation gas.

23. The humidifier of claim 18 wherein said surface active agent coating said light probe is a mixture of sorbitan monoesters which is physiologically compatible with said aqueous liquid and is easily metabolized and has a low degree of toxic reaction.

24. The humidifier of claim 18 wherein said light probe is made of polyacrylate thermoplastic.

25. The humidifier of claim 20 wherein said light probe is subjected to plasma treatment which is physiologically compatible with said aqueous liquid while providing no toxic reaction therewith in order that the surface tension of the light probe is maintained greater than the surface tension of the aqueous liquid to allow the light in said probe to be reflected/not reflected according to the humidifier's needs to thereby maintain sufficiently humidified oxygen or inhalation gas.

26. The humidifier of claim 20 wherein said light probe is subjected to corona discharge treatment which is physiologically compatible with said aqueous liquid while providing no toxic reaction therewith in order that the surface tension of the light probe is maintained greater than the surface tension of the aqueous liquid to allow the light in said probe to be reflected/not reflected according to the humidifier's needs to thereby maintain sufficiently humidified oxygen or inhalation gas.

27. The humidifier of claim 20 wherein at least a portion of interior surfaces of said canister has a surface active agent applied thereto whereby the surface tension of the light probe is maintained greater than the surface tension of the aqueous liquid, to allow the light in said probe to be reflected/not reflected according to the humidifier's needs to thereby maintain sufficiently humidified oxygen or inhalation gas and said surface active agent being physiologically compatible with said aqueous liquid and is easily metabolized and has a low degree of toxic reaction.

28. The humidifier of claim 27 additionally comprising the exterior optical surface of said optical probe having a surface active agent which is physiologically compatible with said aqueous liquid and is easily metabolized and has a low degree of toxic reaction applied thereto to allow the light in said probe to be reflected/not reflected according to the humidifier's needs to thereby maintain sufficiently humidified oxygen or inhalation gas.

29. A removable cannister adapted for use in a humidifier for gases, the humidifer having a closure sealing the cannister, the closure defining a light access port, and transparent probe means communicating with the light access port and extending into the cannister, the transparent probe means defining an end surface within the cannister interior which includes angled surfaces positioned to permit light passing into said transparent probe means toward the end surface to be reflected again up the probe away from the end surface when the end surface is out of contact with aqueous liquid, and the light to be transmitted through the end surface when the probe is in contact with the aqueous liquid, the improvement comprising:

at least a portion of the interior surface of said cannister having been treated with a surface active agent whereby the surface tension of the light probe is maintained greater than the surface tension of the aqueous liquid so that gas bubbles are inhibited from adhering to submerged surfaces of the light probe to allow said light passing therein not to be reflected and so that liquid droplets are also inhibited from adhering to the unsubmerged surfaces of the light probe to allow said light passing therein to be reflected, and said surface active agent which is physiologically compatible, easily metabolized and has a low toxic reaction with said aqueous liquid to allow the light in said probe to be reflected/not reflected according to the humidifier's needs to thereby maintain sufficiently humidified oxygen or inhalation gas.

30. The cannister of claim 29 wherein said surface active agent is a mixture of sorbitan monoesters which is physiologically compatible with said aqueous liquid and is easily metabolized and has a low degree of toxic reaction.

31. The method of treating an exterior optical surface of an optical probe having light passing therein operational with aqueous liquids to provide automatic liquid level sensing, comprising the step of selectively maintaining the surface tension of the optical surface greater than the surface tension of the aqueous liquid used therewith, with a surface active agent which is a physiologically compatible, easily metabolized, low toxic reaction means, thereby inhibiting the adherence of gas bubbles to submerged portions of the optical surface to allow said light passing therein not to be reflected and inhibiting the formation of liquid droplets to unsubmerged portions of the optical surface to allow said light passing therein to be reflected, wherein the selective maintenance of the surface tension of the optical surface greater than the surface tension of the aqueous liquid is provided to maintain a desired liquid level.

32. The method of claim 31 wherein the surface tension of the exterior of the optical surface of said optical probe is maintained greater than the surface tension of the aqueous liquid by applying a coating of surface active agent, which is physiologically compatible with said aqueous liquid and is easily metabolized and has a low degree of toxic reaction, to the exterior of the optical surface of said optical probe.

33. The method of claim 32 in which said surface active agent consists essentially of non-ionic ester of a carbohydrate moiety and an organic monoacid of 8 to 30 carbon atoms which is physiologically compatible with said aqueous liquid and is easily metabolized and has a low degree of toxic reaction.

34. The method of claim 32 in which said surface active agent is a mixture of sorbitan monoesters which is physiologically compatible with said aqueous liquid and is easily metabolized and has a low degree of toxic reaction.

35. The method of claim 31 wherein the surface tension of the exterior of the optical surface of the optical probe is maintained greater than the surface tension of the aqueous liquid by subjecting the optical surface to plasma treatment which is physiologically compatible with said aqueous liquid while providing no toxic reaction therewith.

36. The method of claim 31 wherein the surface tension of the exterior of the optical surface of the optical probe is maintained greater than the surface tension of the aqueous liquid by subjecting the optical surface to corona discharge treatment which is physiologically compatible with said aqueous liquid while providing no toxic reaction therewith.

37. The method of claim 31 wherein the surface tension of the exterior optical surface of the optical probe is maintained greater than the surface tension of the aqueous liquid by adding an amount of surface active agent which is physiologically compatible with said aqueous liquid and is easily metabolized and has a low degree of toxic reaction, to the aqueous liquid.

38. The method of claim 37 in which said surface active agent consists essentially of an ethoxylated non-ionic ester of a carbohydrate moiety and an organic monoacid of 8 to 30 carbon atoms which is physiologically compatible with said aqueous liquid and is easily metabolized and has a low degree of toxic reaction.

39. The method of claim 37 in which said surface active agent is a mixture of ethoxylated sorbitan monoesters which is physiologically compatible with said aqueous liquid and is easily metabolized and has a low degree of toxic reaction.

40. The method of claim 31 wherein the exterior of the optical surface of the optical probe and aqueous liquid are contained in a container and wherein the surface tension of the exterior of the optical surface is maintained greater than the surface tension of the aqueous liquid by applying a coating of surface active agent to at least a portion of the interior surface of the container, to maintain a desired liquid level in the container, said surface active agent being physiologically compatible with said aqueous liquid and is easily metabolized and has a low degree of toxic reaction.

41. The method of claim 40 additionally comprising the step of applying a coating of surface active agent to the exterior of the optical surface.

42. The method of claim 41, wherein the optical probe is made of a hydrophobic thermoplastic material.

43. A cannister adapted for use in a humidifier for gases, the humidifier having a closure sealing the cannister, the closure defining a light access port, and transparent probe means communicating with the light access port and extending into the cannister, the transparent probe means defining an end surface with the cannister interior which includes angled surfaces positioned to permit light passing into said transparent probe means toward the ends surface to be reflected again up the probe away from the end surface when the end surface is out of contact with aqueous liquid, and the light to be transmitted through the end surface when the probe is in contact with the aqueous liquid, the improvement comprising:

said light probe having a surface tension maintained greater than the surface tension of the aqueous liquid by having been treated with a surface active agent whereby gas bubbles in the aqueous liquid are inhibited from adhering to submerged surfaces of the light probe to allow said light passing therein not to be reflected and whereby liquid droplets are inhibited from adhering to unsubmerged portions of the light probe to allow said light passing therein to be reflected and said surface tension being maintained with said surface active agent which is a physiologically compatibile, easily metabolized low toxic reaction means to maintain sufficiently humidified oxygen or inhalation gas.

* * * * *